US00PP20625P2

(12) United States Plant Patent
Perkins

(10) Patent No.: US PP20,625 P2
(45) Date of Patent: Jan. 5, 2010

(54) ***SALVIA* PLANT NAMED 'SALV BULE'**

(50) Latin Name: *Salvia farineacea*
Varietal Denomination: Salv Bule

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/313,048

(22) Filed: Nov. 17, 2008

(51) Int. Cl.
*A01H 5/00* (2006.01)

(52) U.S. Cl. ..... Plt./475

(58) Field of Classification Search ..... Plt./475
See application file for complete search history.

*Primary Examiner*—Kent L Bell
(74) *Attorney, Agent, or Firm*—S. Matthew Edwards

(57) ABSTRACT

A new *Salvia* plant named 'Salv Bule', particularly distinguished by large dark violet-purple flowers and long racemes, early bloomer, strong stems and racemes with dark foliage and a dense habit.

1 Drawing Sheet

Latin name of the genus and species of the plant claimed: *Salvia farineacea.*

Varietal denomination: 'Salv Bule'.

BACKGROUND OF THE NEW PLANT

The present invention comprises a new *Salvia,* botanically known as *Salvia farineacea*, and hereinafter referred to by the variety name 'Salv Bule'.

'Salv Bule' is a product of a planned breeding program. The new cultivar 'Salv Bule' has large dark violet-purple flowers and long racemes, early bloomer, strong stems and racemes with dark foliage and a dense habit.

'Salv Bule' originated from an open pollination in a planned breeding program in Gilroy, Calif. U.S.A. The female parent was an unpatented hybrid seedling identified as 'Il-(7).5' with deep blue color. 'Il-(7).5' has fewer flowers on each raceme, flowers not as flat, and a taller habit than 'Salv Bule.' The male parent of 'Salv Bule' is unknown.

'Salv Bule' was selected as one flowering plant within the progeny of the stated open pollination in April 2006 in a controlled environment in Gilroy, Calif. U.S.A. The pollination took place in July 2005 and the seed sowing in December 2005.

The first act of asexual reproduction of 'Salv Bule' was accomplished using vegetative cuttings from the initial selection in the April 2006 in a controlled environment in Gilroy, Calif. U.S.A.

Horticultural examination of plants grown from cuttings of the plant initiated in April 2006 in Gilroy, Calif. U.S.A., and continuing thereafter, has demonstrated that the combination of characteristics as herein disclosed for 'Salv Bule' are firmly fixed and are retained through successive generations of asexual reproduction.

'Salv Bule' has not been observed under all possible environmental conditions. The phenotype may vary significantly with variations in environment such as temperature, light intensity and day length.

A Plant Breeder's Right for this cultivar was applied for in Canada on Dec. 24, 2007. 'Salv Bule' has not been made publicly available more than one year prior to the filing of this application.

DESCRIPTION OF THE DRAWINGS

The accompanying photographic drawing shows typical flower and foliage characteristics of 'Salv Bule' with colors being as true as possible with an illustration of this type. The photographic drawing shows a flowering potted plant of the new variety and a close-up of the flowers and spike. This plant was grown and photographed in Gilroy, Calif. U.S.A. in April 2008. The plant was about 4 months old.

DETAILED BOTANICAL DESCRIPTION

The measurements were taken in April 2008, in Gilroy, Calif. U.S.A., on plants that were growing in one gallon pots, in a greenhouse trial. This plant was about 4 months old.

Color Chart used: Royal Horticultural Society Colour Chart (R.H.S.) 2001

BRIEF SUMMARY OF INVENTION

The following observations, measurements, and comparisons describe plants grown Gilroy, Calif. U.S.A. The following traits have been repeatedly observed and are determnined to be basic characteristics of the new variety. The combination of these characteristics distinguishes this *Salvia* as a new and distinct variety.

TABLE 1

DIFFERENCES BETWEEN THE NEW CULTIVAR 'SALV BULE' AND A SIMILAR VARIETY

| | 'Salv Bule' | 'Victoria Blue' (Not patented) |
|---|---|---|
| Flower spike habit | Denser with florets | Has fewer florets |
| Plant height | Shorter | Taller |
| Plant habit | More compact | Less compact |

Plant:

*Form, growth and habit.*—Upright, good vigor, dense habit with strong stems and spikes.

*Plant height.*—31–34 cm.

*Plant height* (*inflorescence included*).—46–51 cm.

*Plant width.*—36–40 cm.

Foliage:

*Immature, leaf color, upper surface.*—Between RHS 146A and 146B.

*Lower surface.*—A little darker than RHS 147B.

*Mature, leaf color, upper surface.*—Closest to but darker than RHS 146A.

*Lower surface.*—A little darker than RHS 147B.

*Length.*—7.7–8.9 cm.

*Width.*—3.0–3.8 cm.

*Shape.*—Ovate.

*Base shape.*—Attenuate.

*Apex shape.*—Mucronulate.

*Margin.*—Mostly entire but sometimes have a few lacerations.

*Texture.*—Both surfaces: pubescence on veins and margins.

*Color of veins, upper surface.*—RHS 144B.

*Color of veins, lower surface.*—RHS 144B.

*Petioles color.*—RHS 144B.

*Petioles length.*—3.1–4.3 cm.

*Diameter of petiole.*—0.15–0.2 cm basally.

*Texture.*—Slightly pubescent.

Stem:

*Number of branches/main stems per plant.*—3–4.

*Number of leaves per stem.*—12–14.

*Color of stem.*—RHS 144A; some stems have vertical stripes of between RHS N200A and N200B.

*Length of stem.*—25–28 cm.

*Diameter.*—0.4–0.5 cm.

*Length of internodes.*—4.0–4.7 cm.

*Texture.*—Pubescent; pilose at nodes.

Inflorescence:

*Type.*—Terminal racemes.

*Quantity of florets per inflorescence.*—Over 100 flowers and buds in whorls.

*Lastingness of individual flowers on the plant.*—4–5 days.

*Fragrance.*—Slight.

*Blooming habit.*—Flowers continuously from spring until fall.

*Duration of flowering.*—Continuous flowering throughout the summer.

*Raceme color.*—Closest to RHS 93A but slightly more purple.

*Raceme length.*—11–12.5 cm.

*Raceme diameter.*—0.2 cm.

*Texture.*—Pubescent.

*Color of pedicel.*—Some appear to be RHS 198D and other RHS 86D.

*Length of pedicel.*—0.2–0.3 cm.

*Diameter of pedicel.*—0.05 cm.

*Texture.*—Pubescent.

Corolla:

*Form.*—Single, bilabiate; one upper lip, and one lower lip with three lobes consisting one a mid-lobe and 2 small lateral lobes; lips fused at base; upper lip wraps around the pistil.

*Immature florets general color, upper surface.*—Closest to RHS N89A but more purple and less blue.

*Lower surface.*—RHS N88A.

*Mature florets vertical height of floret.*—0.7–0.9 cm.

*Horizontal width of floret.*—1.0–1.4 cm.

*Depth of floret.*—2.0–2.3 cm.

*Color upper lip, upper surface.*—RHS N89B but appears deeper because of the RHS N89A color of the villous hairs.

*Color upper lip, lower surface.*—RHS 92B.

*Length of upper lip.*—0.3–0.4 cm.

*Width of upper lip.*—0.3–0.4 cm.

*Shape.*—Obovate.

*Apex shape.*—Obtuse.

*Margin.*—Entire.

*Texture, upper surface.*—Villous hairs of RHS N89A.

*Lower surface.*—Glabrous.

*Color lower lip, mid-lobe, upper surface.*—RHS N89B; developing blotches of RHS N155A or RHS 94D as the lip matures.

*Color lower lip, mid-lobe, lower surface.*—RHS 92B.

*Length of lower lip, mid-lobe.*—0.7–1.0 cm.

*Width of lower lip, mid-lobe.*—0.6–0.7 cm.

*Shape.*—Obovate.

*Apex shape.*—Rounded.

*Margin.*—Very slightly praemorse.

*Texture, upper surface.*—Papillose.

*Lower surface.*—Glabrous.

*Color lower lip, lateral lobe, upper surface.*—Closest to RHS N88B.

*Color lower lip, lateral lobe, lower surface.*—RHS 92B.

*Length of lower lip, lateral lobe.*—0.4–0.5 cm.

*Width of lower lip, lateral lobe.*—0.25–0.3 cm.

*Shape.*—Oblong.

*Apex shape.*—Obtuse.

*Margin.*—Entire.

*Texture, upper surface.*—Papillose.

*Lower surface.*—Glabrous.

*Corolla, color, outer surface.*—RHS N89B with RHS 91D basally.

*Inner surface.*—RHS 91D.

*Texture.*—Glabrous on both surfaces.

Bud (just before opening):

*Color.*—RHS N89B at apex with RHS N88B to N88C basally.

*Length.*—0.6–0.8 cm.

*Width.*—0.3–0.4 cm.

*Shape.*—Slightly obovate.

Calyx:

*Number of sepals.*—2, fused into a tube form.

*Color of sepals.*—RHS N88A at the apex; pubescence color RHS N91D basally.

*Length of sepals.*—0.5–0.6 cm.

*Width of sepals.*—0.4 cm.

*Sepal shape.*—Slightly oblanceolate.

*Apex shape.*—Acute.

*Margin.*—Entire.

*Texture, outer surface.*—Heavily pubescent.

*Inner surface.*—Glabrous.

Reproductive organs:

*Pistil.*—1.

*Length.*—1.0–1.2 cm.

*Style color.*—RHS N155A; sericeous hairs of RHS 91A to 91B.

*Style length.*—0.9–1.0 cm.

*Stigma color.*—RHS 94C.

*Stamens.*—2.

*Color of filaments.*—RHS N155A.

*Anther color.*—RHS 11A.

*Anther length.*—0.1 cm.

*Color of pollen.*—RHS 13B.

*Pollen amount.*—Moderate.

*Fertility/seed set.*—Not observed on this hybrid.

Disease/pest resistance: Disease resistance or susceptibility has not been observed on this hybrid.

What is claimed is:

1. A new and distinct variety of *Salvia* plant named 'Salv Bule', substantially as illustrated and described herein.

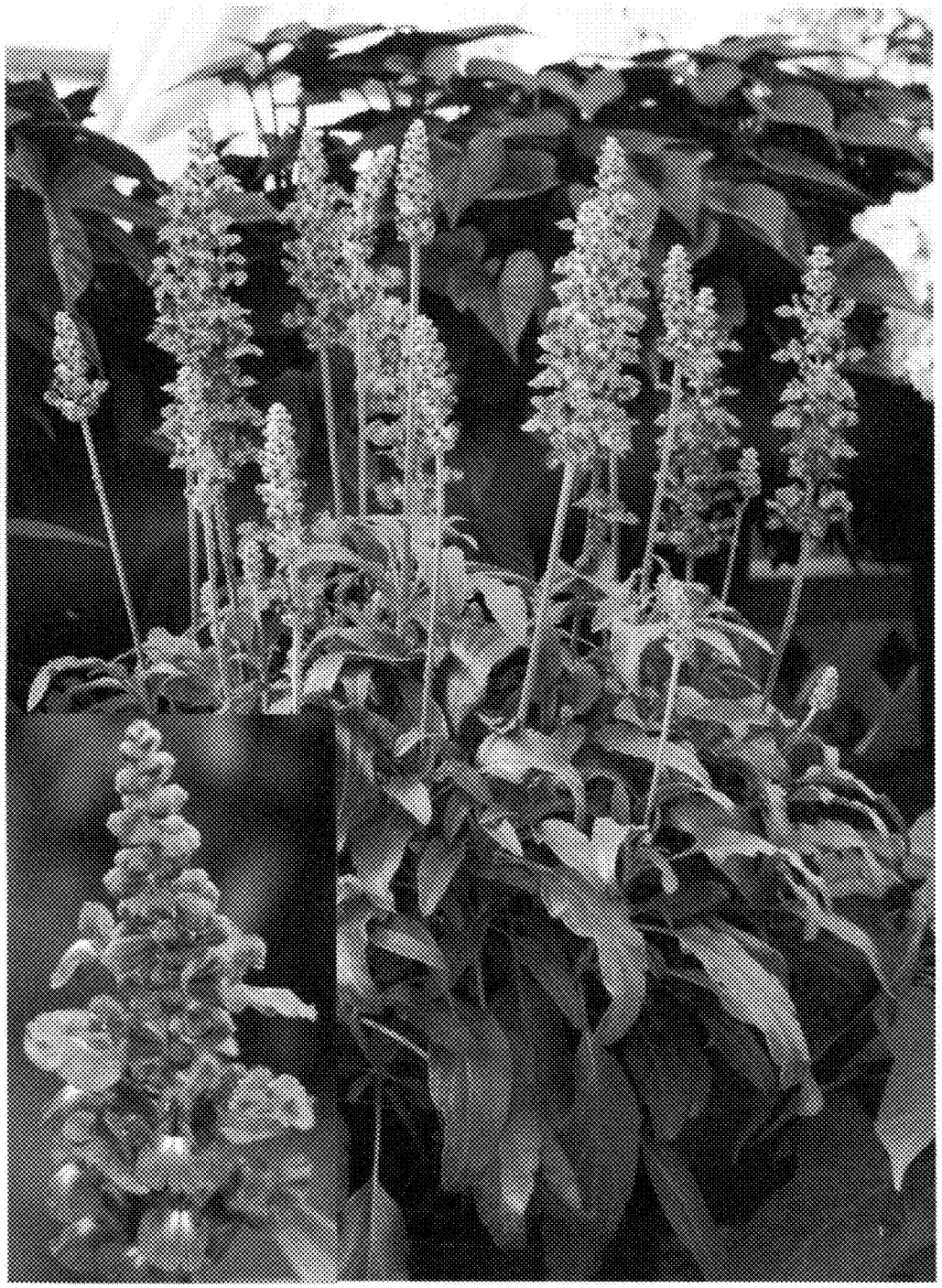

* * * * *